(12) United States Patent
Yayon

(10) Patent No.: US 6,447,783 B1
(45) Date of Patent: Sep. 10, 2002

(54) COMPOSITIONS COMPRISING FGF9 AND USE THEREOF FOR STIMULATING CARTILAGE AND BONE REPAIR

(75) Inventor: Avner Yayon, Moshav Sitria (IL)

(73) Assignee: Yeda Research and Development Co., Ltd. (IL)

( * ) Notice: Subject to any disclaimer, the term of this patent is extended or adjusted under 35 U.S.C. 154(b) by 0 days.

(21) Appl. No.: 08/981,030

(22) PCT Filed: Jun. 12, 1996

(86) PCT No.: PCT/IL96/00011
§ 371 (c)(1),
(2), (4) Date: May 6, 1998

(87) PCT Pub. No.: WO96/41523
PCT Pub. Date: Dec. 27, 1996

Related U.S. Application Data
(60) Provisional application No. 60/000,137, filed on Jun. 12, 1995.

(51) Int. Cl.$^7$ .............................................. A61K 39/00
(52) U.S. Cl. .................... 424/198.1; 530/350; 530/351; 530/399; 514/12; 536/23.5
(58) Field of Search .................................. 530/350, 351, 530/399; 514/12; 424/198.1; 536/23.5

(56) References Cited

U.S. PATENT DOCUMENTS

| | | | |
|---|---|---|---|
| 5,270,197 A | 12/1993 | Yayon et al. | 435/240.2 |
| 5,512,460 A | * 4/1996 | Nauro et al. | 435/69.1 |
| 5,571,895 A | 11/1996 | Kurokawa et al. | 530/399 |

FOREIGN PATENT DOCUMENTS

| EP | 0 608 546 A2 | 8/1994 |
|---|---|---|

OTHER PUBLICATIONS

Garofalo, S. t al. "Skeletal Dysplasia and Defective Chondrocyte Differentiation by targeted Overexpression of Fibroblast Growth Factor 9 in Transgenic Mice", Journal of Bone and Mineral Research, vol. 14, No. 11, pp. 1909–1915, 1999.*
Spivak–Kroizman, T., et al. "Heparin–Induced Oligomerization of FGF Molecules is Responsible for FGF Receptor Dimerization, Activation, and Cell Proliferation". Cell, vol. 79, pp. 1015–1024, Dec. 1994.*
Chellaiah et al., "Fibroblast Growth Factor Receptor (FGFR) 3," The Journal of Biological Chemistry 269(15):11620–11627, 1994.
Dionne et al., "Cloning and expression of two distinct high–affinity receptors cross–reacting with acidic and basic fibroblast growth factors," The EMBO Journal 9(9):2685–2692, 1990.
Givol et al., "Complexity of FGF receptors: genetic basis for structural diversity and functional specificity," FASEB J. 6:3362–3369, 1992.
Johnson et al., "Structural and Functional Diversity in the FGF Receptor Multigene Family," Advances in Cancer Research 60:1–41, 1993.
Keegan et al., "Isolation of an additional member of the fibroblast growth factor receptor family, FGFR–3," Proc. Natl. Acad. Sci. USA 88:1095–1099, 1991.
Naruo et al., "Novel Secretory Heparin–binding Factors from Human Glioma Cells (Glia–activating Factors) Involved in Glial Cell Growth," The Journal of Biological Chemistry 268(4):2857–2864, 1993.
Peters et al., "Unique Expression Pattern of the FGF Receptor 3 Gene during Mouse Organogenesis," Developmental Biology 155:423–430, 1993.
Rimoin, "Prenatal Abnormal Bone Growth: A Perspective," In Normal and Abnormal Bone Growth: Basic and Clinical Research, Proceedings of the Second Int'l Conference held at the University of California Center for the health Sciences, Los Angeles, CA, Jan. 3–5, 1985, Dixon and Sarnat (eds.) Alan R. Liss, Inc.: New York, pp. 131–140, 1985.
Rousseau et al., "Mutations in the gene encoding fibroblast growth factor receptor–3 in achondroplasia," Nature 371:252–254, 1994.
Yayon et al., "Cell Surface, Heparin–like Molecules Are Required for Binding of Basic Fibroblast Growth Factor to Its High Affinity Receptor," Cell 64:841–848, 1991.
Miyamoto, M., et al., "Molecular Cloning of Novel Cytokine cDNA Encoding the Ninth Member of the Fibroblast Growth Factor Family, Which Has a Unique Secretion Property", Molecular and Cellular Biology, vol. 13 (1993), pp. 4251–4259.
Lev, S., et al., "Dimerization and Activation of the Kit Receptor by Monovalent and Bivalent Binding of the Stem Cell Factor", The Journal of Biological Chemistry, vol. 267 (1992), pp. 15970–15977.
Ornitz, D., M. and Leder, P., "Ligand Specificity and Heparin Dependence of Fibroblast Growth Factor Receptors 1 and 3", The Journal of Biological Chemistry, vol. 267 (1992), pp. 16305–16311.
Hecht, D. et al., "Identification of Fibroblast Growth Factor 9 (FGF9) as a High Affinity, Heparin Dependent Ligand for FGF Receptors 3 and 2 but not for FGF Receptors 1 and 4", Growth Factors, vol. 12 (1995), pp. 223–233.
Santos–Ocampo, S., Expression and Biological Activity of Mouse Fibroblast Growth Factor–9:, The Journal of Biological Chemistry, vol. 271 (1996), pp. 1726–1731.

\* cited by examiner

Primary Examiner—Lorraine Spector
Assistant Examiner—Eileen B. O'Hara
(74) Attorney, Agent, or Firm—Fish & Richardson P.C.

(57) ABSTRACT

The invention provides murine and chicken FGF9 polypeptides and recombinant DNA sequences encoding them. Also included in the invention are compositions containing FGF9 or an agent that binds to FGF9, e.g., an antibody that binds to FGF9, and methods of using FGF9 and the compositions to stimulate cartilage or bone repair. The invention also encompasses a transgenic mouse containing a transgene encoding FGF9.

7 Claims, 14 Drawing Sheets

Figure 4A:
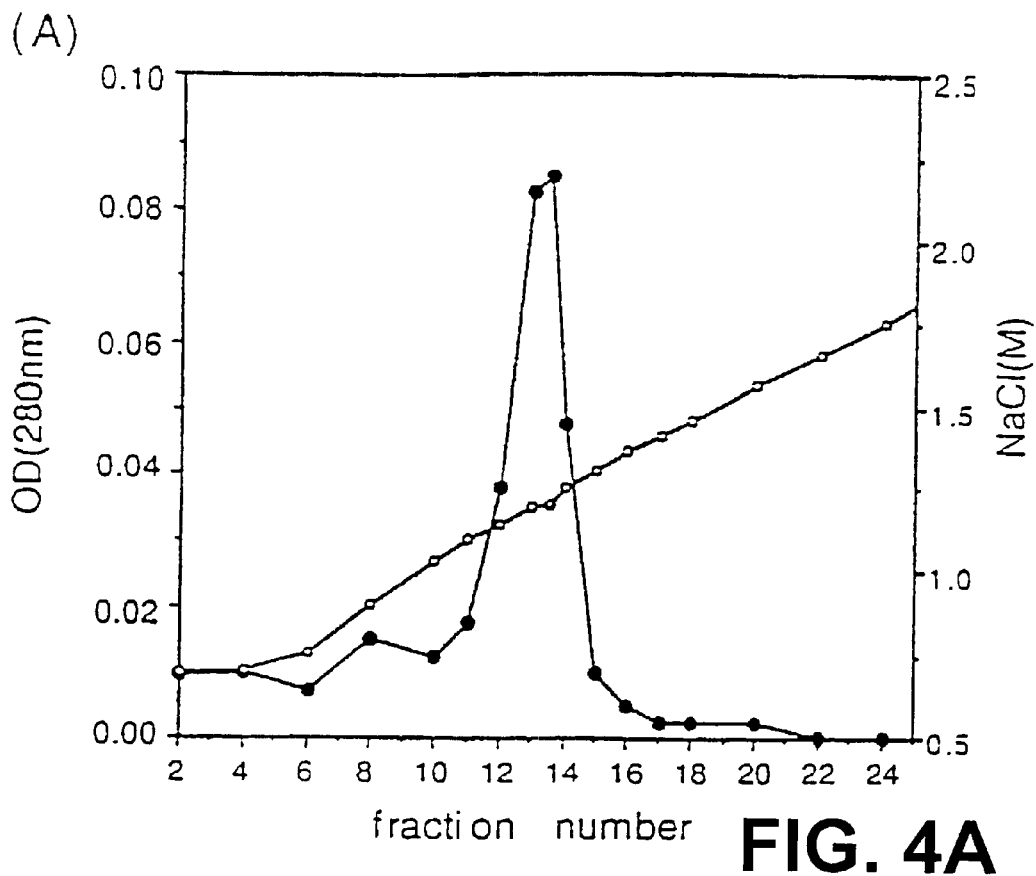

```
  1   ACAACGGTTCCCTCTAGAAATAATTTGTTTAACTTTAAGAAGGAGATATACATATGGC       60
                                                             M  A

61   TCCCTTAGTGAAGTTGGGAGCTATTTCGGTGTGCAGGACGCGGTACCGTTCGGGAACGT     120
       P  L  G  E  V  G  S  Y  F  G  V  Q  D  A  V  P  F  G  N  V

121   ACCGGTGTTGCCGGTGTGGACAGTCCGGTGTTGCTAAGTGACCACCTGGGTCAGTCCGAAGC   180
       P  V  L  P  V  D  S  P  V  L  S  D  H  L  G  Q  S  E  A

181   AGGGGGGCTGCCCCGGGGCCCCGCAGTGACTCACGGACTTGGATCATTTAAAGGGGATTCTCAG  240
       G  G  L  P  R  G  P  P  A  V  T  D  L  D  H  L  K  G  I  L  R

241   GCGGAGGCAGCTGTACTGCAGGACTGGATTTCATTTAGAGATCTTCCCCAACGGTACTAT    300
       R  R  Q  L  Y  C  R  T  G  F  H  L  E  I  F  P  N  G  T  I

301   CCAGGGAACCAGGAAAGACCACTCTTCCAACCTCTCTGGAATTTATCAGTATAGCAGT     360
       Q  G  T  R  K  D  H  S  R  F  G  I  L  E  F  I  S  I  A  V

361   GGGCCTGGTCAGCATTCGCGGTGTGGACAGTCTACCTCGGCATGAACGAGAAGG          420
       G  L  V  S  I  R  G  V  D  S  G  L  Y  L  G  M  N  E  K  G

421   GGAGCTGTATGGATCAGAAAAACTAACACAGGAATGTGTTCAGAGAACAGTTTGAAGA     480
       E  L  Y  G  S  E  K  L  T  Q  E  C  V  F  R  E  Q  F  E  E

481   GAACTGGTACAACAACTACTCTTCCAACCTCTATAAACATGTGGACACCGGAAGGAGATA   540
       N  W  Y  N  T  Y  S  S  N  L  Y  K  H  V  D  T  G  R  R  Y

541   CTATGTTGCATTAAATAAGGACGGGACTCCAAGAGAAGGGACTAAACGGCACCA         600
       Y  V  A  L  N  K  D  G  T  P  R  E  G  T  R  T  K  R  H  Q

601   GAAATTTACACATTTTTTACCTAGACCCTGACAAAGTACCTGAACTATATAA           660
       K  F  T  H  F  L  P  R  P  V  D  P  D  K  V  P  E  L  Y  K

661   GGATATTCTAAGCCAAAGTTGA    682  (SEQ ID NO: 1)
       D  I  L  S  Q  S  *          (SEQ ID NO: 3)
```

FIG. 1

| | 10 | 20 | 30 | 40 | 50 | 60 |
|---|---|---|---|---|---|---|
| 1f33_cf9-sp6 5 2 | CCGCGGGATT P R D <== | GGGAATTCCA W E F | TATGGCTCCC H M A P | TTAGGTGAAG L G E | TCGGGAACTA V G N Y | TTTCGGTGTG F G V |

| | 70 | 80 | 90 | 100 | 110 | 120 |
|---|---|---|---|---|---|---|
| 1f33_cf9-sp6 5 2 | CAGGACGCGG Q D A <== | TGCCCTTTGG V P F G | GAACGTGCCC N V P | GCGCTGCCGG A L P | CGGACAGCCC A D S P | GGTTTTGCTC V L L |

| | 130 | 140 | 150 | 160 | 170 | 180 |
|---|---|---|---|---|---|---|
| 1f33_cf9-sp6 5 2 | AGTGACCACC S D H <== | TGGGCCAGGC L G Q A | TGAGGCAGGT E A G | GGGcTGCCCA G L P | GGGGCCCCGC R G P A | GGTCACGGAC V T D |

| | 190 | 200 | 210 | 220 | 230 | 240 |
|---|---|---|---|---|---|---|
| 1f33_cf9-sp6 5 2 | TTGGACCATT L D H <== | TAAAGGGGAT L K G I | CcTCAGGAGG L R R | AGGCAGcTTT R Q L | ACTGCAGGAC Y C R T | TGGATTTCAT G F H |

| | 250 | 260 | 270 | 280 | 290 | 300 |
|---|---|---|---|---|---|---|
| 1f33_cf9-sp6 5 2 | TTAGAAATCT L E I <== | TCCCCAATGG F P N G | TACTATCCAG T I Q | GGCACCAGGC G T R | AAGACCACAG Q D H S | CCGATTCGGT R F G |

| | 310 | 320 | 330 | 340 | 350 | 360 |
|---|---|---|---|---|---|---|
| 1f33_cf9-sp6 5 2 | ATACTGGAGT I L E <== | TCATCAGTAT F I S I | AGCAGTGGGC A V G | CTGGTCAGCA L V S | TCCGAGGAGT I R G V | AGACAGCGGA D S G |

| | 370 | 380 | 390 | 400 | 410 | 420 |
|---|---|---|---|---|---|---|
| 1f33_cf9-sp6 5 2 | CTCTACCTTG L Y L <== | GAATGAATGA G M N E | AAAAGGGGAG K G E | CTCTACGGCT L Y G | CGGAAAAATT S E K L | AACCCAGGAG T Q E |

| | 430 | 440 | 450 | 460 | 470 | 480 |
|---|---|---|---|---|---|---|
| 1f33_cf9-sp6 5 2 | TGTGTATTCA C V F <== | GAGAGCAGTT R E Q F | TGAAGAAAAC E E N | TGGTATAACA W Y N | CATATTCATC T Y S S | AAATCTATAT N L Y |

| | 490 | 500 | 510 | 520 | 530 | 540 |
|---|---|---|---|---|---|---|
| 1f33_cf9-sp6 5 2 | AAACACGTGG K H V <== | ACACTGGAAG D T G R | ACGATACTAC R Y Y | GTGGCGTTAA V A L | ATAAAGATGG N K D G | AACTCCAAGA T P R |

| | 550 | 560 | 570 | 580 | 590 | 600 |
|---|---|---|---|---|---|---|
| 1f33_cf9-sp6 5 2 | GAAGGGACTA E G T <== | GGACTAAACG R T K R | GCATCAAAAA H Q K | TTTACACATT F T H | TTTCACCTAG F S P R | ACCAGTGGAC P V D |

| | 610 | 620 | 630 | 640 | 650 | 660 |
|---|---|---|---|---|---|---|
| 1f33_cf9-sp6 5 2 | CCTGAGAAAG P E K <== | TACCTGAACT V P E L | ATATAAGGAT Y K D | ATTcTAAGCC I L S | AAAGTTGAGG Q S J G | ATCCCGAATC S R I (SEQ ID NO: 4) (SEQ ID NO: 5) |

FIG. 2

```
fgf9rat   MAPLGEVGSY   FGVQDAVPFG   NVPVLPVDSP   VLLSDHLGQS     40
fgf9mou   MAPLGEVGSY   FGVQDAVPFG   NVPVLPVDSP   VLLSDHLGQS     40
fgf9hum   MAPLGEVGNY   FGVQDAVPFG   NVPVLPVDSP   VLLSDHLGQS     40 fgf9rat   EAGGLPRGPA   VTDLDHLKGI   LRRRQLYCRT   GFHLEIFPNG     80
fgf9mou   EAGGLPRGPA   VTDLDHLKGI   LRRRQLYCRT   GFHLEIFPNG     80
fgf9hum   EAGGLPRGPA   VTDLDHLKGI   LRRRQLYCRT   GFHLEIFPNG    80 fgf9rat   TIQGTRKDHS   RFGILEFISI   AVGLVSIRGV   DSGLYLGMNE    120
fgf9mou   TIQGTRKDHS   RFGILEFISI   AVGLVSIRGV   DSGLYLGMNE    120
fgf9hum   TIQGTRKDHS   RFGILEFISI   AVGLVSIRGV   DSGLYLGMNE    120 fgf9rat   KGELYGSEKL   TQECVFREQF   EENWYNTYSS   NLYKHVDTGR    160
fgf9mou   KGELYGSEKL   TQECVFREQF   EENWYNTYSS   NLYKHVDTGR    160
fgf9hum   KGELYGSEKL   TQECVFREQF   EENWYNTYSS   NLYKHVDTGR    160 fgf9rat   RYYVALNKDG   TPREGTRTKR   HQKFTHFLPR   PVDPDKVPEL    200
fgf9mou   RYYVALNKDG   TPREGTRTKR   HQKFTHFLPR   PVDPDKVPEL    200
fgf9hum   RYYVALNKDG   TPREGTRTKR   HQKFTHFLPR   PVDPDKVPEL    200 fgf9rat   YKDILSQS  *208  (SEQ ID NO: 10)
fgf9mou   YKDILSQS  *208  (SEQ ID NO: 3)
fgf9hum   YKDILSQS  *208  (SEQ ID NO: 11)
```

FIG. 3A

FIG. 3B (SEQ ID NO: 12)
(SEQ ID NO: 2)
(SEQ ID NO: 13)

FIG. 3C

```
fgf9rat  AAGGGGAGC TGTATGGATC AGAAAAACTA ACACAGGAGT  400
fgf9mou  AAGGGGAGC TGTATGGATC AGAAAAACTA ACACAGGAAT  400
fgf9hum  AAGGGGAGC TGTATGGATC AGAAAAACTA ACCCAAGAGT  400 fgf9rat  GCGTGTTCAG AGAACAGTTT GAAGAAAACT GGTACAAACAC  440
fgf9mou  GTGTGTTCAG AGAACAGTTT GAAGAGAAACT GGTACAAACAC  440
fgf9hum  GTGTATTCAG AGAACAGTTC GAAGAAAACT GGTATAATAC  440 fgf9rat  CTACTCTTCC AACCCTGACA AGCACGTGGA CACCGGAAGG  480
fgf9mou  CTACTCTTCC AACCCTCTCA AACATGTGGA CACCGGAAGG  480
fgf9hum  GTACTGGTCA AACCCTATATA AGCACGTGGA CACTGGAAGG  480 fgf9rat  AGATACTATG TTGCATTAAA TAAGGATGGG ACTCCAAGAG  520
fgf9mou  AGATACTATG TTGCATTAAA TAAGGATGGG ACTCCAAGAG  520
fgf9hum  CGATACTATG TTGCATTAAA TAAAGATGGG ACCCCGAGAG  520 fgf9rat  AAGGGACCAG GACTAAAACGG CACCCAGAAAT TTACACATTT  560
fgf9mou  AAGGGACCAG GACTAAAACGG CACCAGAAAAT TTACACATTT  560
fgf9hum  AAGGGACTAG GACTAAAACGG CACCAGAAAT TCACACATTT  560 fgf9rat  TTTACCTAGA CCAGTGGACC CTGACAAAGT ACCTGAACTA  600
fgf9mou  TTTACCTAGA CCAGTGGACC CTGACAAAGT ACCTGAACTA  600
fgf9hum  TTTACCTAGA CCAGTGGACC CGACACAAAGT ACCTGAACTG  600 fgf9rat  TATAAGGATA AAGTTGA 627  (SEQ ID NO: 12)
fgf9mou  TATAAGGATA AAGTTGA 627  (SEQ ID NO: 2)
fgf9hum  TATAAGCCA AAGTTGA 627  (SEQ ID NO: 13)
```

(A)

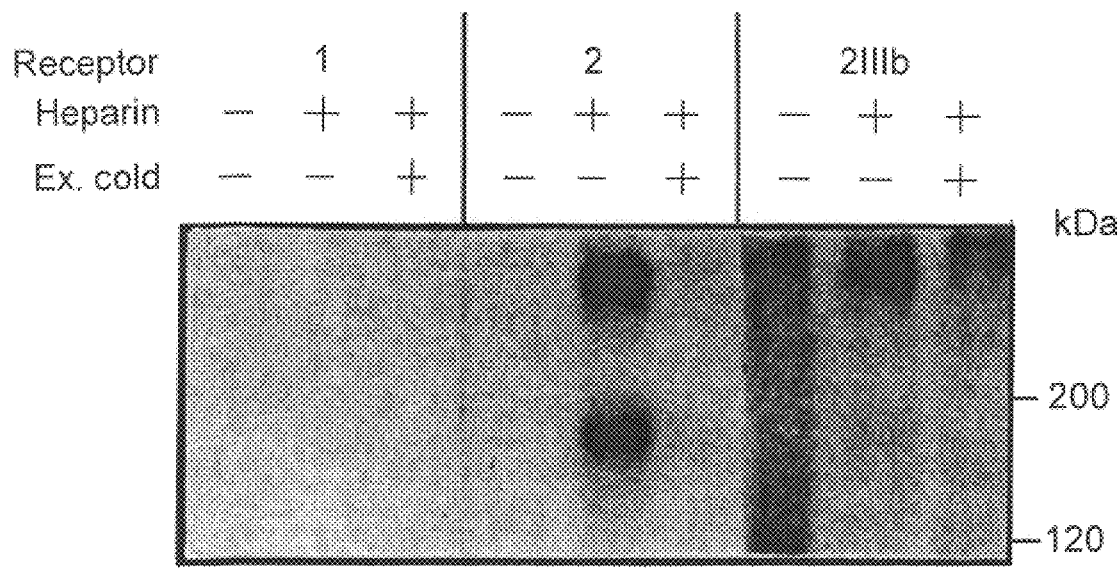
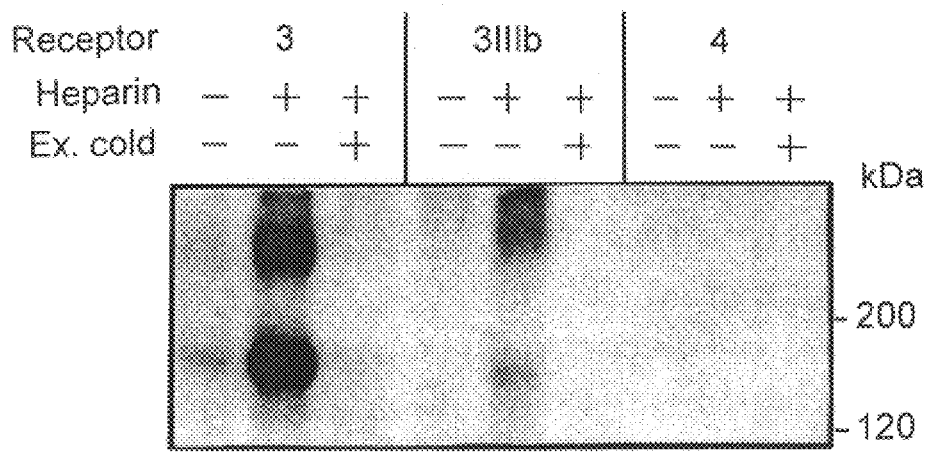
FIG. 5B

US 6,447,783 B1

COMPOSITIONS COMPRISING FGF9 AND USE THEREOF FOR STIMULATING CARTILAGE AND BONE REPAIR

This application is the National Stage of International Application No. PCT/IL96/00011, filed Jun. 12, 1996, which claims priority of U.S. Provisional Application No. 60/000, 137, filed Jun. 12, 1995.

FIELD OF THE INVENTION

The present invention concerns fibroblast growth factor 9 (FGF9), a novel high affinity ligand for fibroblast growth factor receptor 3 (FGFR3), methods for detecting FGFR3 using said ligand and pharmaceutical compositions for modulating FGFR3 activity comprising FGF9, an antagonist thereof, or FGF9 binding-agents.

BACKGROUND OF THE INVENTION

Fibroblast growth factors (FGF) comprise a family of at least nine multifunctional polypeptides involved in a variety of biological processes including morphogenesis, angiogenesis and tissue remodeling. They stimulate the proliferation of cells from mesenchymal to epithelial and neuroectodermal origin. FGFs share structural similarity, but differ in their target specificity and spatial and temporal expression pattern. Four FGF receptor (FGFR) genes encoding transmembrane protein tyrosine kinases, have been cloned and identified in mammals and their homologues described in birds, Xenopus and Drosophila (Givol and Yayon, *FASEB J.*, 6:33622269 (1992)). The actual number of functional receptor proteins is however much greater since multiple variants are generated, as cell bound or secreted forms, by alternative RNA splicing and multiple polyadenylation sites. Beside these high affinity receptors, FGFs bind tightly to low affinity, high capacity binding sites identified as heparan sulfate proteoglycans (HSPGs). These heparan sulfates modulate FGF-receptor binding and biological activity and serve as an obligatory integral component in the formation of a functional tertiary complex between FGF, FGFR and the appropriate HSPG.

In light of the large number of ligand and receptor variants, a major question regarding FGF function is their ligand-receptor specificity. Both FGFR1 and FGFR2 bind acidic FGF/FGF1 and basic FGF/FGF2 with similar affinity (Dionne et al., *EMBO J.*, 9:2685–2692 (1990)). In fact all FGFRs tested so far bind FGF1 and FGF4 (hst/kfgf) with moderate to high affinity, demonstrating an apparent redundancy in the FGF system. In contrast to FGFRs 1 and 2, FGFR3 was found to bind only FGF1 and FGF4 albeit with moderate affinity (Ornitz and Leder, *J. Biol. Chem.*, 267:16305–16311 (1992); Chellaiah et al., *J. Biol. Chem.*, 269(15):11620–11622, (1994)). No specific ligand has been identified so far, for either of the spliced forms of this receptor.

Recently, mutations in FGFR3 have been shown to be responsible for achondroplasia, the most common form of genetic dwarfism. Examination of the sequence of FGFR3 in achondroplasia patients identified a mutation in the transmembrane domain of the receptor.

The focus of FGFR3 as the receptor involved in achondroplasia raised the need for a specific ligand for this receptor, which does not substantially bind to the other three FGFRs, both for the purpose of research and study of this disease as well as for the purpose of developing possible medicaments for its treatment.

A heparin-binding, glia-activating factor purified from the culture supernatant of a human glioma cell-line was found, by a homology search, to be the ninth member of the FGF family and was thus termed FGF9. Human FGF9 was found to code for a 208 amino acid protein and presents a unique spectrum of biological activity as it stimulates the proliferation of glial cells, PC-12 cells and BALB/C 3T3 fibroblasts, but nevertheless is not mitogenic for endothelial cells (Miyamote et al., *Mol. Cell. Biol.*, 13(7):4251–4259 (1993); Naro et al., *J. Biol. Chem.*, 267:16305–16311 (1993)).

SUMMARY OF THE INVENTION

The present invention is based on the surprising finding their fibroblast growth factor 9 (FGF9) is a high affinity (kD: 0.25 nM) ligand for fibroblast growth factor receptor 3 (FGFR3) which does not bind to FGFR1 or FGFR4 and binds to FGFR2 only at a substantially lower affinity.

Thus, the present invention provides for the first time a specific ligand for FGFR3 being a fibroblast growth factor 9 (FGF9). This specific FGFR3 ligand may be used both for detection and for therapeutical treatment purposes.

This specific novel ligand for FGFR3 may be used in a method for the detection of FGFR3 in a sample or tissue comprising:

(i) contacting the sample or tissue with FGF9 and allowing formation of receptor-ligand pairs, and (ii) detecting the presence of FGFR3-FGF9 pairs, a positive detection indicating the presence of FGFR3 in the sample or tissue.

The sample may be a sample of body fluid such as blood, in which soluble FGFR3 is present and the tissue may be a tissue obtained from a patient, for example by cartilage biopsy or alternatively, may be a tissue within the body of an individual and in such a case the detection is carried out in vivo.

Detection may be carried out for example by labelling the FGF9 with a suitable detectable label, and then determining whether any label is bound to proteins in the sample or to the surface of cells in the tissue which is assayed for the presence of FGFR3. Alternatively detection may be carried out by using labeled antibodies against FGF9, capable of recognizing FGF9 which is bound of FGFR3.

In accordance with the present invention, it was found that FGF9 is a heparin-dependent ligand for FGFR3. Thus, in accordance with the method of detection of FGFR3 by use of the FGF9 ligand, it is preferable that heparin would also be present in the detection medium.

In accordance with the present invention, it was further found that FGF9 not only specifically binds to the FGFR3, but also specifically activates this receptor without activating the FGFR1 and FGFR4 receptors and, if appropriate concentrations are chosen, without significantly activating FGFR2. This finding leads to the preparation of pharmaceutical compositions comprising a pharmaceutically acceptable carrier and as an active ingredient a therapeutically effective amount of FGF9. Such a pharmaceutical compositions may be used for stimulating the activity of FGFR3.

This finding also leads to the preparation of pharmaceutical compositions comprising a pharmaceutically acceptable carrier and as an active ingredient an antagonist of the FGF9, or an FGF9 binding agent an example being an antibody against FGF9.

Pharmaceutical compositions comprising an antagonist of FGF9 may be used to attenuate directly the activity of the FGFR3, and pharmaceutical compositions comprising an FGF9 binding agent such as an antibody against FGF9, may neutralize circulating native FGF9 and thus attenuate indirectly the activity of FGFR3.

Normal cartilage and bone growth and repair of damage to the cartilage and bone requires a specific and delicate balance between up regulation and down regulation of the activity of the FGFR3. Without wishing to be bound by theory, it is assumed that active FGFR3 is necessary in the initial stages of cartilage-bone differentiation, and after differentiation is required for cartilage-bone repair. Thus, the pharmaceutical composition comprising as an active ingredient FGF9, which stimulates the activity of FGFR3, may be used in order to encourage cartilage and bone repair, for example by administration to the site of injury. Furthermore, FGFR3 exists usually temporarily on mesenchymal stem cells and usually disappears after differentiation. Administration of FGF9 may serve to stabilize FGFR3 and thus prolong the period in which it is active prior to differentiation. FGF9 has also a chemotactic affect of FGFR3-carrying cells and can promote migration of such FGFR3 carrying cells, typically mesenchymal stem cells, to a desired site, for example, by injection of FGF9 to the growth plate top of the column.

According to this theory, overactivation of FGFR3 after the stage of initial differentiation of bone and cartilage cells, leads to halted growth, and is probably the cause of achondroplasia. Thus, a pharmaceutical composition comprising as an active ingredient an antagonist of FGF9 which attenuates the activity of FGFR3, or comprising an FGF9 binding agent (such as an antibody against FGF9), which neutralizes native circulating FGF9, should be used in cases of overactivity of the FGFR3 receptor in differentiated tissues, which causes bone and cartilage growth arrest. Such bone and cartilage growth arrest may lead to achondroplasia dwarfism, or other abnormalities of bone and cartilage growth, for example, multiple hereditary exostosis, solitary hereditary exostosis, hallux valgus deformity, synovial chondromatosis and endochondromas.

The above conditions may be treated with a pharmaceutical composition comprising either an antagonist of FGF9, or an FGF9 binding agents capable of neutralizing native circulating FGF9, which both serve to attenuate the activity of the FGFR3.

The present invention also concerns a novel recombinant mouse FGF9, and a novel recombinant chicken FGF9, as well as DNA sequences coding for these novel recombinant proteins.

The present invention still further concerns an expression vector comprising the sequence of FGF9 under the expression control of a strong promoter such as the CMV or SV40 or a cartilage/bone promoter such as collagen type-2 promoter. Such an expression vector may be used to produce a transgenic mammal, which over-expresses FGF9 leading to overactivation of the FGFR3 receptor and thus to halted growth. Such an animal may serve as a model for diseases and disorders resulting from halted growth, such as genetic achondroplasia.

In the following the invention will be illustrated with reference to some non-limiting drawings and examples.

DETAILED DESCRIPTION OF THE DRAWINGS

FIG. 1—Nucleotide and amino acid sequences of mouse FGF9. The nucleotide sequence (SEQ ID NO:2) of FGF9:pET-3C and deduced amino acid sequence SEQ ID NO:3 are shown.

FIG. 2—Nucleotide and amino acid sequences of chicken FGF9. The nucleotide sequence SEQ ID NO:4 of FGF9 pET-3C and deduced amino acid sequence SEQ ID NO:5 are shown. Nucleotides 22 to 645 of SEQ ID NO:4 encode chicken FGF9. The amino acid sequence of chicken FGF9 extends from amino acid residue 8 to amino acid residue 215 of SEQ ID NO:5.

FIGS. 3A, 3B, 3C shows comparison of amino acid (SEQ ID NO:3, SEQ ID NO:10 and SEQ ID NO:11) and nucleotide (SEQ ID NO:2, SEQ ID NO:12, and SEQ ID NO:13) sequences of mouse, rat and human FGF9 respectively.

FIG. 4—Purification of FGF9. Partially purified FGF9 was bound to heparin sepharose and eluted with a 0.2–2 M salt gradient, protein amount was estimated by spectrophotometer (A). To identify FGF9 in the elution fractions, 10 ml of each fraction were resolved in 15% SDS PAGE, transferred to nitrocellulose and immunoblotted with specific antibodies (anti SP32) (B). The purity of the fractions was tested by silver staining of 5 ml of each fraction resolved on 15% SDS PAGE (C).

FIG. 5—FGF9 binding specificity. Purified FGF9 was immobilized on heparin sepharose beads and its ability to bind the soluble extracellular domain of different FGFRs coupled to alkaline phosphatase was tested (A). The amounts of FGFRs were estimated according to alkaline phosphatase activity (B). Equal amounts of soluble extracellular domain of FGFRs 1, 2, 2-IIIb, 3, 3-IIIb and 4 alkaline phosphatase fusion proteins, were immunoprecipitated with anti alkaline phosphatase antibodies. Binding and cross-linking of $^{125}$I-FGF9 in the presence or absence of 0.5 μg/ml heparin and hundred fold excess unlabeled FGF9 (Ex. cold) was done as described under materials and methods.

FIG. 6—Analysis of FGF9 binding to soluble FGFR2 and FGFR3. Binding of increasing concentrations of $^{125}$I-FGF9 to soluble extracellular domain of FGFR2 (A) and FGFR3 (B) adsorbed to maxisorb plate was done as described under materials and methods. Binding results were analyzed by Scatchard analysis (inserts).

Figure 7:
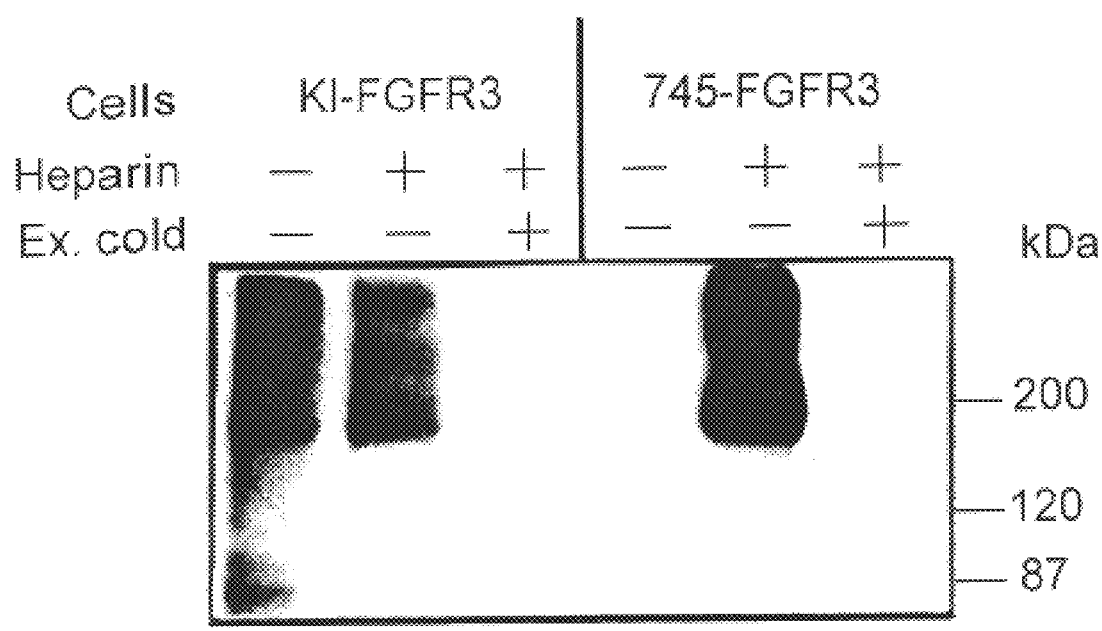

FIG. 7—Heparin dependent cross-linking of FGF9 to FGFR3 expressing CHO cells. Monolayers of FGFR3 transfected KI and A745 CHO cells were incubated at 40° C. with 5 ng/ml $^{125}$I-FGF9 in the presence or absence of 1 mg/ml heparin and 100-fold excess of unlabeled FGF9 (Ex. cold) as indicated. Cross-linking and electrophoresis separation were done as described under materials and methods.

Figure 8A:
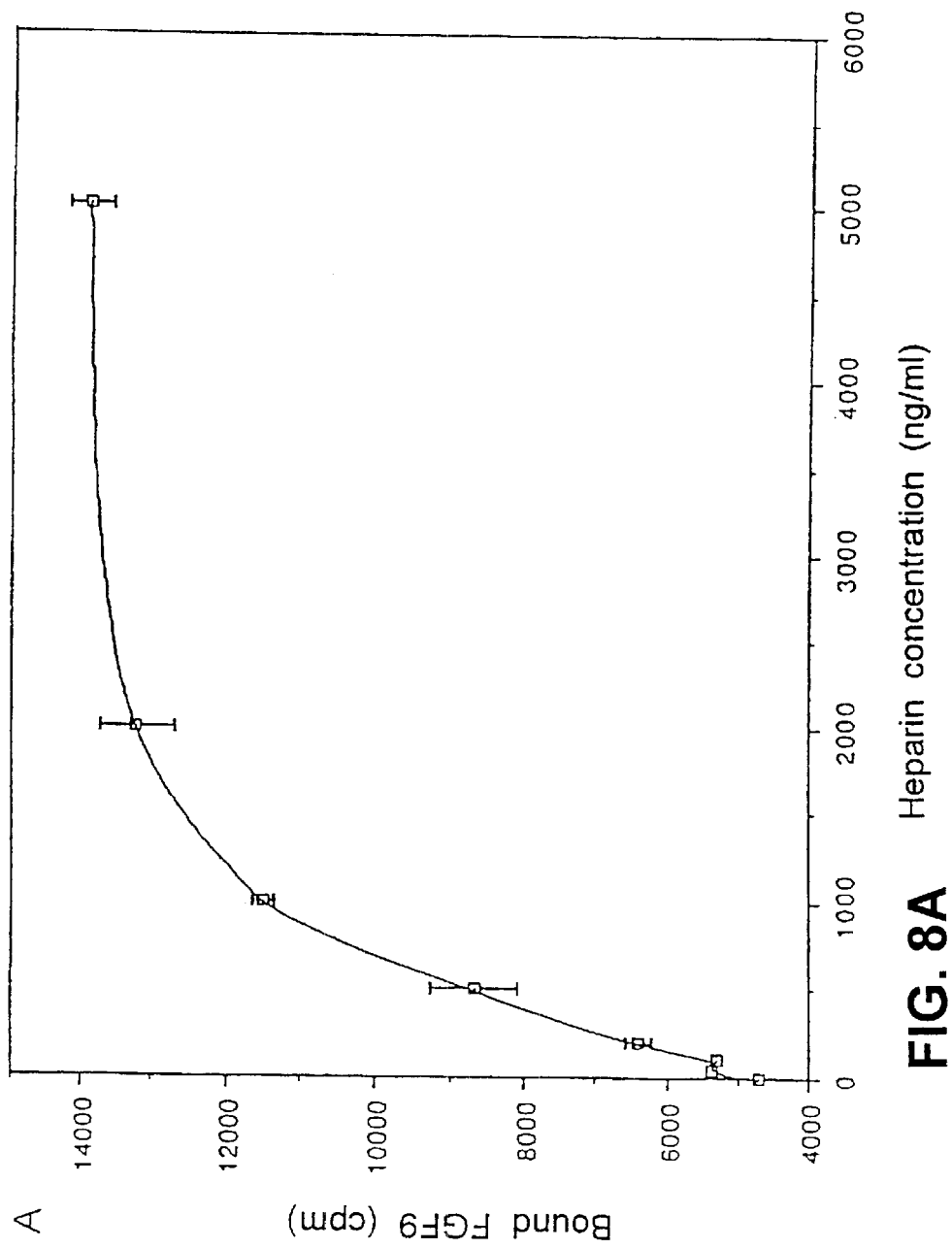

FIG. 8—Heparin and heparin fragments dependent FGF9 induced DNA synthesis. Monolayers of FGFR3 transfected CHO-A745 cells were serum starved and incubated with 10 ng/ml FGF9 and the indicated amount of heparin (A) or 2 mg/ml of heparin fragment (B) at the indicated number of monosaccharide units.

Figure 9:
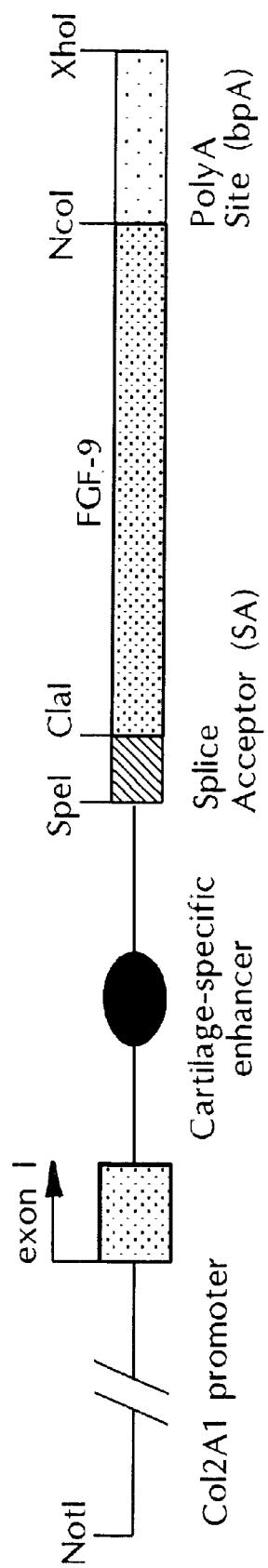

FIG. 9—Plasmid of FGF9 under control of collagen type-2 promoter.

DETAILED DESCRIPTION OF THE INVENTION

1. Materials and Methods (a) Cells.

Wild type (KI) and the CHO mutant cell line A745 kindly provided by Dr. J. D. Esko (Dept. of Biochemistry, University of Birmingham, Ala.) were cultured in F12 medium supplemented with 10% Fetal Calf Serum. Transfection of CHO cells with 10 μg FGFR3 is pZL plasmid that contain neomycin resistance, was done by electroporation with Gene Pulcer (Bio-Rad) at 960 micro farads and 250 volt. Individual stable clones were selected with G418 (0.5 mg/ml).

(b) Antibodies

Polyclonal anti FGF9 antibodies were generated by injecting New Zealand white rabbits and collecting serum after two additional boosts. Anti FGF9 antibodies were prepared against two peptides (SP31: Cys-Ser-Asn-Leu-Tyr-Lys-His-Val-Gln-Thr-Gly-Arg-Arg-Tyr, (SEQ ID NO:6) SP32: Asp-His-Leu-Lys-Gly-Ile-Leu-Arg-Arg-Arg-Gln-Leu-Tyr-Cys (SEQ ID NO:7)) coupled to KLH (keyhole lympet hemocyanin) by MBS. Serum obtained was further purified on protein A sepharose (Repligen) to obtain the IgG fraction.

(c) Radiolabeling of FGF9

Recombinant murine FGF9 was labeled with Na$^{125}$I(0.5 mCi) using the Chloramine-T method and separated from free iodine on a heparin-sepharose column. The range of specific activity was 0.5–2×10$^5$ cpm/ng.

EXAMPLE 1

Cloning and Expression of the Mouse Homologue of FGF9

Total RNA extracted from a 12.5 day old mouse embryo was used for polymerase chain reaction (PCR) based cloning of FGF9. Primer specific for the human FGF9 (forward: GGGAATTCCATATGGCTCCCTTAGGTGAAG; (SEQ ID NO:8) backward: CGGGATCCTCAACTTTGGCTTA-GAATATCC (SEQ ID NO:9)) were used for PCR using as a template mouse RNA, (35 cycles of denaturation 1 min at 94° C., annealing 2 min at 56° C., elongation 3 min at 72° C.). A single DNA product with an expected size of 630 bp was obtained and was used directly for subcloning into pET-3C bacterial expression vector (Novagene).

Sequence analysis reveals the expected 627 bp long transcript (FIG. 1) with 93% identity to the human FGF9 cDNA. The FGF9:pET-3C plasmid was used to transform B1-21 strain of E. coli. At logarithmic growth phase the transformed bacteria were induced with 1 mM IPTG for 2 hours, precipitated by centrifugation at 7000 RPM and sonicated 3×15" using probe sonicator (Soniprep150, MSE) on ice. The supernatant obtained by centrifugation of the bacterial sonicate was loaded onto a heparin-sepharose column (Pharmacia, Upsala, Sweden) and the column was washed extensively with 10 column volumes of 0.15 M NaCl, 0.05% Chaps, 20 mM Tris pH 7.4, and 10 column volumes of 0.7 M NaCl, 0.05% Chaps, 20 mM Tris pH 7.4. The bound proteins were then eluted with 0.5 ml fractions of 2 M NaCl, 0.05% Chaps, 10 mM Tris pH 7.4, diluted 1:10 with H$_2$O and reloaded on a pre-equilibrated 1 ml heparin-sepharose mini FPLS column (Pharmacia, Upsala, Sweden). After extensive wash the column was eluted with a continuous 0.2–2 M NaCl gradient and the protein profile determined by adsorbance at 280 nM. The fractions were tested for biological activity measured as 3H-thymidine incorporation into BALB/c-3T3 fibroblasts and for specificity by Western blot using polyclonal antibodies generated in rabbits against FGF9 specific peptides. A major protein band at the expected molecular weight of 27 kDal was obtained that reacted specifically with two different anti-peptide antibodies specific for FGF9.

Figure 4B:
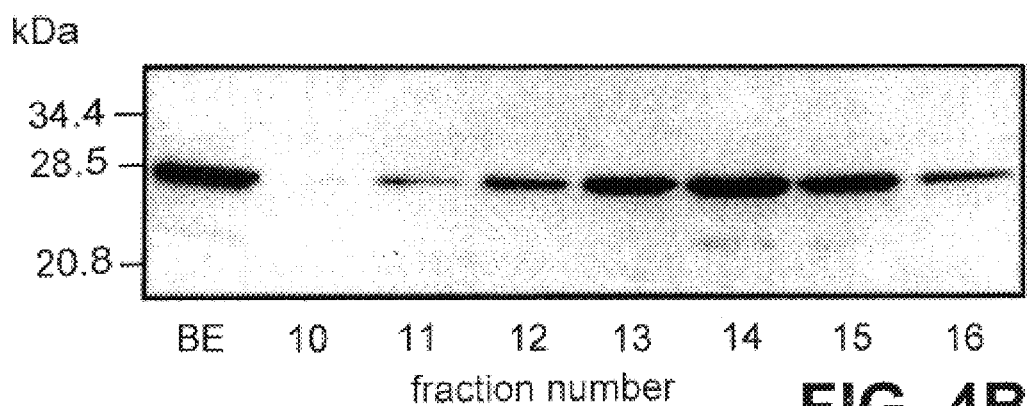
Figure 4C:
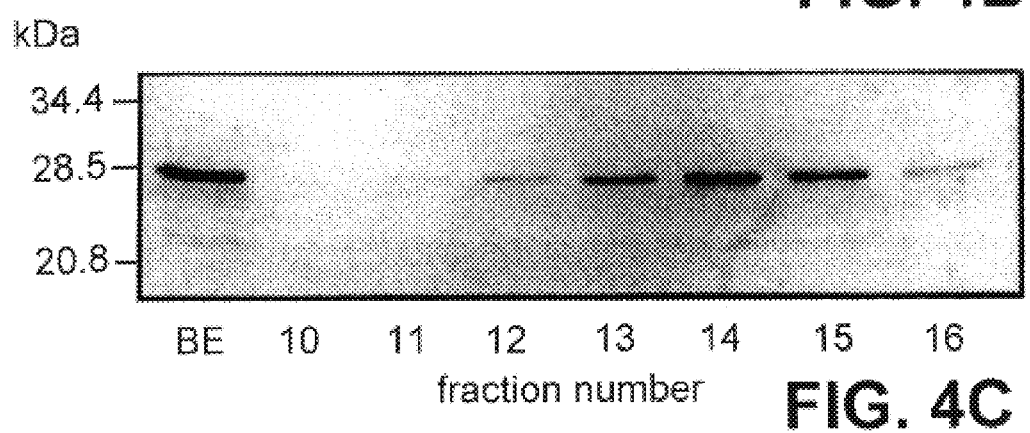

Mouse FGF9 (mFGF9) was cloned by PCR on cDNA prepared from 12.5 days mouse embryos RNA. Mouse FGF9 cDNA shares 93 and 98% sequence homology with human and rat FGF9 respectively (FIGS. 3A–3C). The amino acid sequence of mFGF9 is identical to that of the rat FGF9 and differs from human FGF9 in one amino acid only having a serine at position 9 instead of an asparagine. Recombinant mouse-FGF9 was expressed in B1-21 strain of E. coli and purified from the bacteria lysate by two cycles on a heparin-sepharose column. FGF9 elutes from heparin sepharose with 1.0–1.2 M NaCl as determined by adsorbance at 280 nM (FIG. 4A). The presence of FGF9 in the fractions was tested by an immunoblot using polyclonal antibodies directed against FGF9 specific peptides, demonstrating a major protein band at the expected molecular weight for a non-glycosylated protein of 27 kDal (FIG. 4B). The purity of each preparation was further assessed by silver stain (FIG. 4C). Recombinant mouse FGF9 is biologically active and stimulates DNA synthesis in BALB/C 3T3 fibroblasts, in a dose dependent manner, with half maximal 3H-Thymidine incorporation at 0.5 ng/ml (not shown), similar to that obtained for purified human FGF9 (Nauro, et al., J. Biol. Chem., 267:16305–16311 (1993)).

EXAMPLE 2

Cloning and Expression of the Chicken Homologue of FGF9

Cloning and expression of chicken homologue of FGF9 was conducted as described in Example 1 with chicken-derived mRNA.

EXAMPLE 3

Cell Free Binding Assays

The extracellular region of murine FGFR1, FGFR2, keratinocyte growth factor receptor (KGFR) and the two isoforms of FGFR3 in the alkaline phosphatase-expression vector were previously described (Givol D. and Yayon A., Adv. Cancer Res. 160, 1–41 (1993); (Lev et al, J. Biol. Chem., 267, 15970–15977 (1992)). FGFR-alkaline phosphatase fusion proteins were collected from conditioned medium of transfected NIH 3T3 cells and used directly for binding assays. Receptor protein content was estimated by alkaline phosphatase activity which was monitored spectrophotometrically at 405 nm using para-nitrophenyl phosphate as a substrate, essentially as described (Lev et al., supra). The soluble receptor binding reaction mixture included receptor-AP conditioned medium, radiolabeled ligand and heparin or other HSPGs. The bound complex was immunoprecipitated with anti-alkaline phosphatase polyclonal antibodies (Zymed) and protein A-Sepharose (Repligen). All components are mixed at room temperature in a total volume of 250 ml of binding buffer (DMEM supplemented with 25 mM Hepes pH 7.4 and 0.1% bovine serum albumin). The binding reaction was allowed to proceed for 2 h at room temperature. Bound ligand was recovered by centrifuging for 10 s at 6000 rpm in a microcentrifuge (~2000 g) and washing three times with a solution of 150 nM NaCl, 0.1% Triton-X-100 and 50 mM Hepes pH 7.4 (HNTG). $^{125}$I-bound factor was determined by counting the tubes directly in a gamma-counter. For cross-linking, after washing 0.15 mM disuccinimidyl suberate (DSS) or 1 mM Bis (sulfosuccinimidyl)suberate (BS3) was added in phosphate buffered saline (PBS) for 30 min at room temperature. The complexes were washed twice with PBS, and boiled for 5 min with sample buffer. The samples were separated by electroporation under reducing conditions on SDS-polyacrylamide gel, the gel was dried and exposed to Kodak (Eastman Kodak Co., Rochester, N.Y.) X-Omat AR film.

Alternatively, 96-well maxisorb plates (Nunk) pre-coated overnight with monoclonal anti-human placental alkaline phosphatase antibodies (Sigma Chemicals, Isreal) were reacted with receptor-AP fusion proteins for 2 h at room temperature. After washing with binding buffer, plates were incubated for 2 h at room temperature with different concentrations of $^{125}$I-labeled FGF9 in the presence or absence of heparin. At the end of the incubation time, the plates were washed twice with binding buffer, and eluted with 1.6 M NaCl in 20 mM sodium acetate pH 4.5. The acid extract was counted in a gamma counter.

Figure 5A:
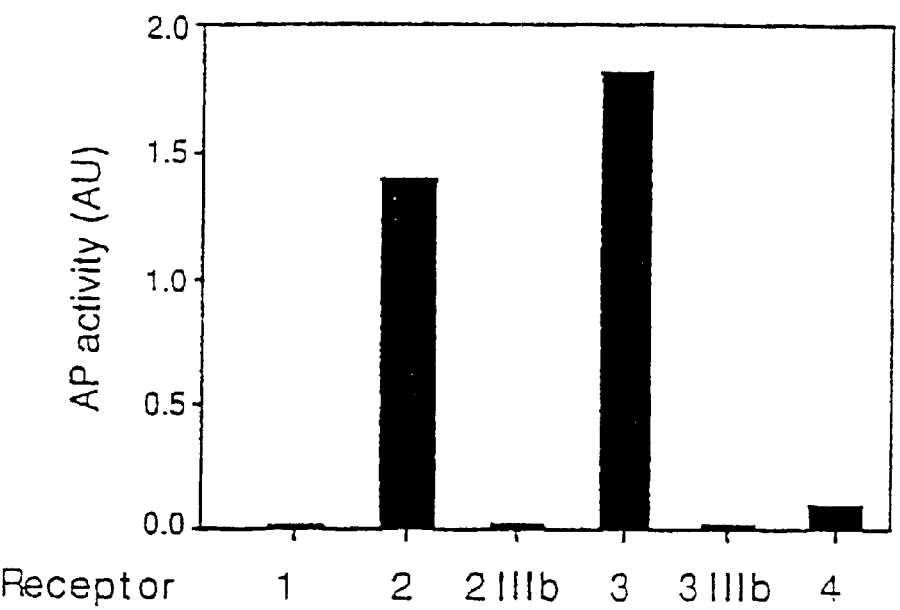

In order to elucidate the receptor binding properties of FGF9, use was made of a series of FGF receptors' ectodomains coupled to human placental alkaline phosphatase. As was previously demonstrated, soluble ectodomains of FGF receptors can successfully and specifically interact with the ligands, thereby providing an excellent tool for the analysis of ligand-receptor specificity (Rimion, D. L., Prof. Clin. Biol. Res. 187, 131–140 (1985), Lev et al, supra). The interaction between FGF9 and the soluble receptors was first analyzed with FGF9 immobilized on heparin-sepharose and measurement of the associated alkaline phosphatase activity. Heparin-sepharose immobilized FGF9 binds FGFR2 and FGFR3 fusion proteins but not FGFR1 or FGFR4 (FIG. 5A). Only the IIIc isoforms of FGFR2 and FGFR3 bind FGF9, while the IIIb isoforms of these receptors do not show any specific binding to FGF9. The interaction of FGF9 with the soluble receptors was further analyzed by direct binding and covalent cross-linking of radiolabeled FGF9 (FIG. 5B). In the presence of 0.5 mg/ml heparin, FGF9 binds only to FGFR2 and FGFR3 but not to FGFR1 or FGFR4 and not to any of the IIIb spliced isoforms tested. No significant binding is observed without heparin, indicating its obligatory role in high affinity FGF9-receptor binding. The two covalently linked complexes of FGF9 with FGFR2 and FGFR3 correspond most probably to the monomer and dimer forms of the receptor-ligand complex. Affinity labeling of soluble FGFR2 and FGFR3 proteins by $^{125}$I-FGF9 is abolished in the presence of a 100 fold molar excess of unlabeled ligand, indicating that binding and labeling of these receptors is specific.

Figure 6A:
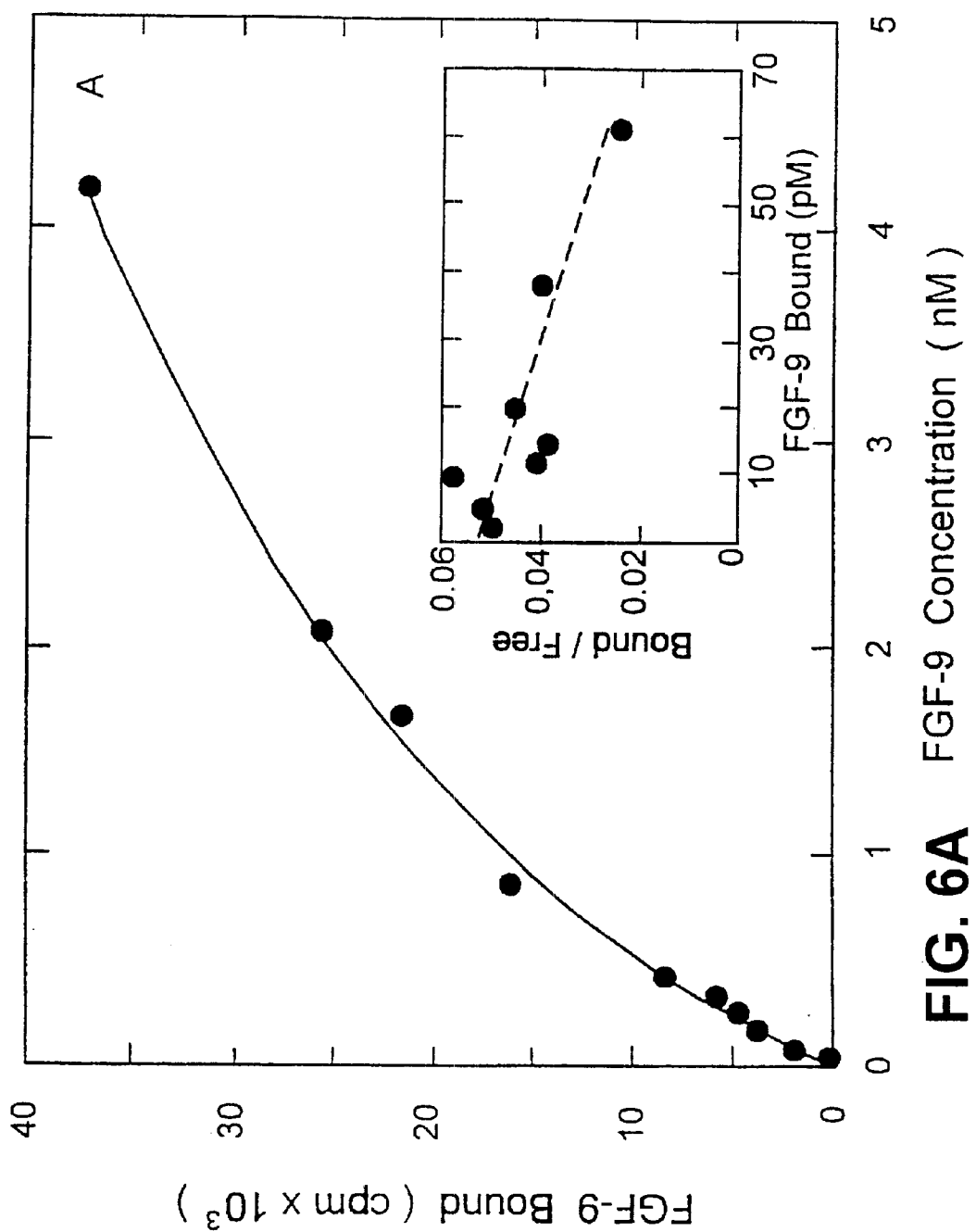
Figure 6B:
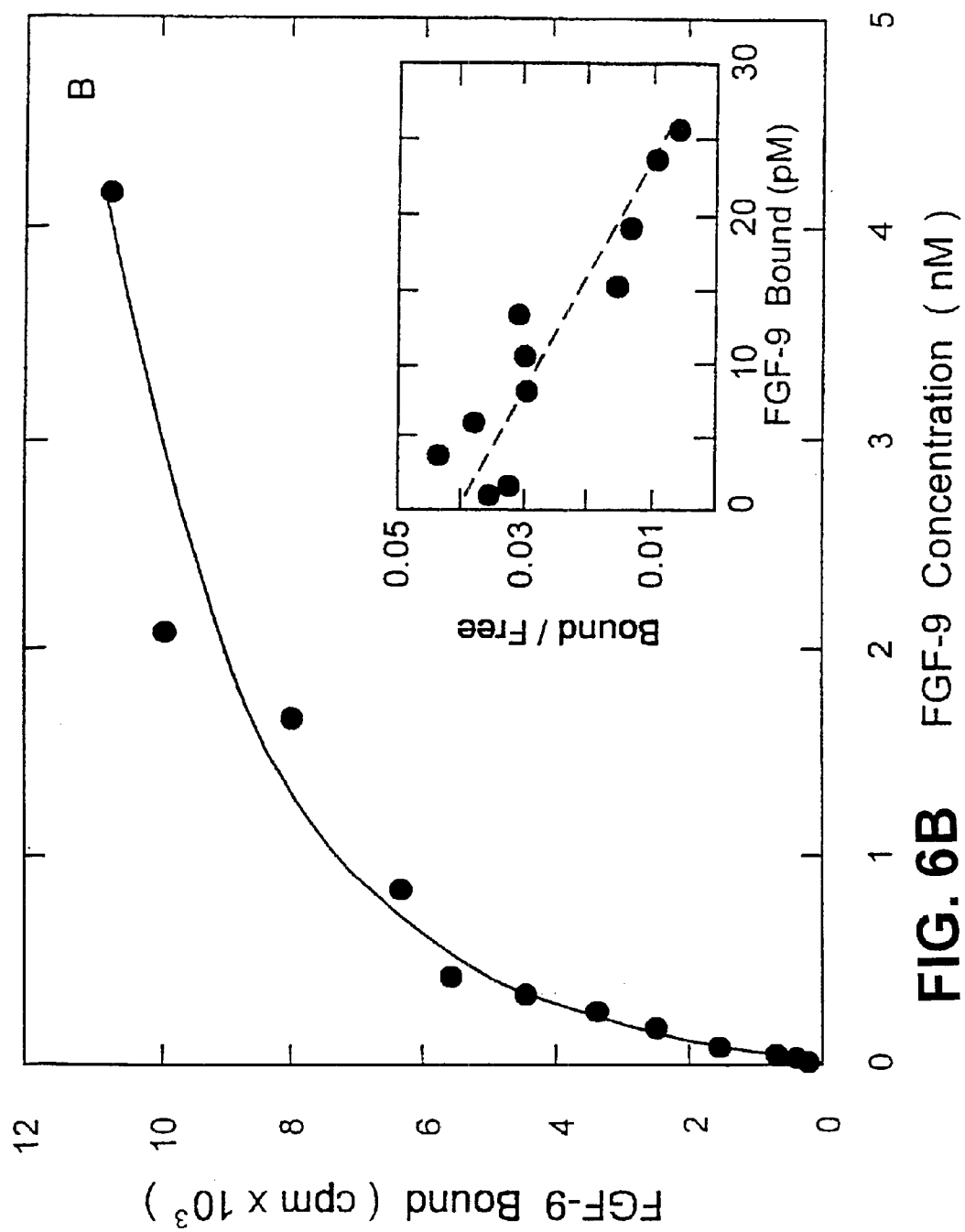

To quantitatively characterize the binding of FGF9 to FGFR2 and FGFR3, direct binding analysis of radiolabeled FGF9 to the soluble receptors was performed. Binding of FGF9 to both receptors is specific and saturable (FIGS. 6A and 6B). Analyzing the results by Scatchard analysis (FIG. 6, inserts) indicate a dissociation constant of 2.38 nM for binding of FGFR2 and 0.78 nM for the interaction of FGF9 with FGFR3. Two additional experiments yield very similar results. Within every single experiment the affinity for FGFR2 was about 3-fold lower compared to that for FGFR3. The binding of FGF9 to FGFR1 was neither significant nor specific (not shown).

EXAMPLE 4

High Affinity Binding and Cross-linking of FGF9 to Cell Surface Receptors

Confluent cultures in 24 wells dishes (Nunk) were pre-cooled to 4° C. and washed twice with binding buffer. Subsequently they were incubated for 2 h at 4° C. with different concentrations of $^{125}$I-FGF9 in binding buffer in the presence or absence of heparin. The binding medium was discarded, and the cells were washed twice with binding buffer and once with 0.5 M NaCl in 25 mM Hepes pH 7.5. High affinity bound factor was determined by eluting the bound factor with 1.6 M NaCl in 20 mM sodium acetate pH 4.5 and counting in a gamma counter. Nonspecific binding was considered as the valuable obtained for high affinity binding in the presence of a 100-fold excess of non-labeled factor. For cross-linking, the binding was done in PBS and after 1 h incubation, DSS was added to a final concentration of 0.15 M for 1 h more. The cells were washed twice with PBS, scraped, and lysed in a small volume of lysis buffer containing 150 mM NaCl, 20 mM Tris (pH 8.0), 1 mM MgCl$_2$, 0.1 mM ZnCl$_2$, 0.5% NP-40, 1 mg of aprotinin, 1 mg/ml leupeptin, and 2 mM PMSF. The cell lysates, clarified by centrifugation, were boiled and electrophorated under reducing conditions on SDS-polyacrylamide gel.

As mentioned above, the binding of FGF9 to both FGFR2 and FGFR3 is strictly dependent on the presence of heparin. To compare the specific demands for heparin in FGF9 binding to each receptor, we first measured the heparin required for binding of FGF9 to soluble FGFR3 and FGFR2. In cross-linking experiments only faint complexes are observed without the addition of heparin to either FGFR2 or FGFR3. However, at increasing heparin concentrations a marked difference in the requirement for heparin the two receptors is observed.

The soluble extracellular domains of FGFR2 and FGFR3 coupled to alkaline phosphatase, were immunoprecipitated with anti-alkaline phosphatase antibodies, and incubated with 5 ng/ml $^{125}$I-FGF9 and increasing concentrations of heparin. Cross-linking and electrophoresis separation were done as described under Example 3. The amount of FGF9 bound to FGFR2 (FIG. 5A) and FGFR3 (FIG. 5B) was quantitated by densitometry analysis.

Binding of FGF9 to FGFR2 is very sensitive to heparin and addition of as little as 0.5 ng/ml heparin causes an apparent increase in binding, with maximal receptor binding at around 5 ng/ml. Binding of FGF9 to FGFR3 however, requires about 20-fold higher levels of free heparin, with maximal receptor binding only at around 100 ng/ml heparin, and with a slight inhibition of binding at heparin concentrations above 500 ng/ml.

A difference in the heparin levels required for FGF9 binding to either FGFR2 or FGFR3, might indicate that a more specific heparin structure, which comprises a relatively minor fraction of the heparin mixture which was used, is required for FGFR3 binding. To study structural requirements of heparin for promoting FGF9 binding, we analyzed the effects of a series of heparin fragments ranging in size from 4 to 18 monosaccharide units, on FGF9 binding to the soluble ectodomains of FGFR2 and FGFR3.

In order to address the physiological relevance of the in vitro observed high affinity, heparin-dependent interaction of FGF9 with FGFR3, a full length mouse FGFR3 was expressed in wild type (KI) and heparan-sulfate deficient mutant (745 pgs) CHO cells, known to express low levels of endogenous FGFRs (Yayon, A., et al., Cell, 64:841–848 (1991). Whereas untransfected cells displayed neither detectable binding of radiolabeled FGF9 nor covalently cross-linked proteins, FGFR3 transfected CHO-KI cells show a protein band of a 145 kDal, corresponding to a monomer of receptor-FGF9 complex (FIG. 7). As expected, binding and cross-linking of $^{125}$I-FGF9 to wild type CHO-KI cells expressing FGFR3 is not affected by exogenous heparin. There is however not detectably, cross-linking of FGF9 to the mutant HS defficient CHO-745 cells expressing FGFR3 in the absence of heparin (FIG. 7), supporting the notion that heparin-like molecules are required for efficient high affinity interaction of FGF9. Upon the addition of heparin affinity labeling of the 745-FGFR3 cells with $^{125}$I-FGF9 is prominent and indistinguishable from that of wild type cells, indicating that heparin can support high affinity binding of FGF9 to FGFR3. The binding to both kinds of cells was specific and saturable (in the presence of 1 mg/ml heparin) with kD of 0.06 and 0.1 nM for CHO-KI and CHO 745 cells respectively. A typical heparin dose dependent increase in FGF9 binding to CHO 745-FGFR3 transfected cells was obtained, with maximal specific binding at around 500 ng/ml of heparin (data not shown).

EXAMPLE 5

DNA Synthesis Assay

Tymidine incorporation into CHO cells was measured using confluent cultures grown in 24 well plates, in F12 medium supplemented with 10% fetal calf serum. The cells were starved for 24 h with no serum and then incubated with or without various concentrations of FGF9 or 10% serum as a control for an additional 14 h, after which 3H-Thymidine (0.5 mCi/ml) was added for additional 24 h. At the end of the incubation, the cells were washed twice with cold PBS, fixed for 20 min with ice-cold 5% trichloroacetic acid, washed with 95% ethanol and dissolved in 0.1 M NaOH. DNA associated radioactivity was measured by liquid scintillation counting.

To test whether activation of FGFR3 may also require heparin, we investigated the requirement for heparin for FGF9 induced DNA synthesis in FGFR3 expressing HS-defficient CHO 745 cells. Without exogenous heparin no significant increase in 3H-Thymidine incorporation by FGF9 is observed (FIG. 8A), in agreement with the lack of receptor binding and similar to the strict heparin requirement for other FGFs investigated so far. Addition of heparin at low concentrations markedly stimulated FGF9 dependent DNA synthesis and in a dose dependent manner with half maximal and maximal effects at 100 ng/ml and 2 mg/ml respectively. Heparin alone had no effect on DNA synthesis and FGF9 induced DNA synthesis in CHO-KI is independent of exogenous heparin (not shown).

Figure 8B:
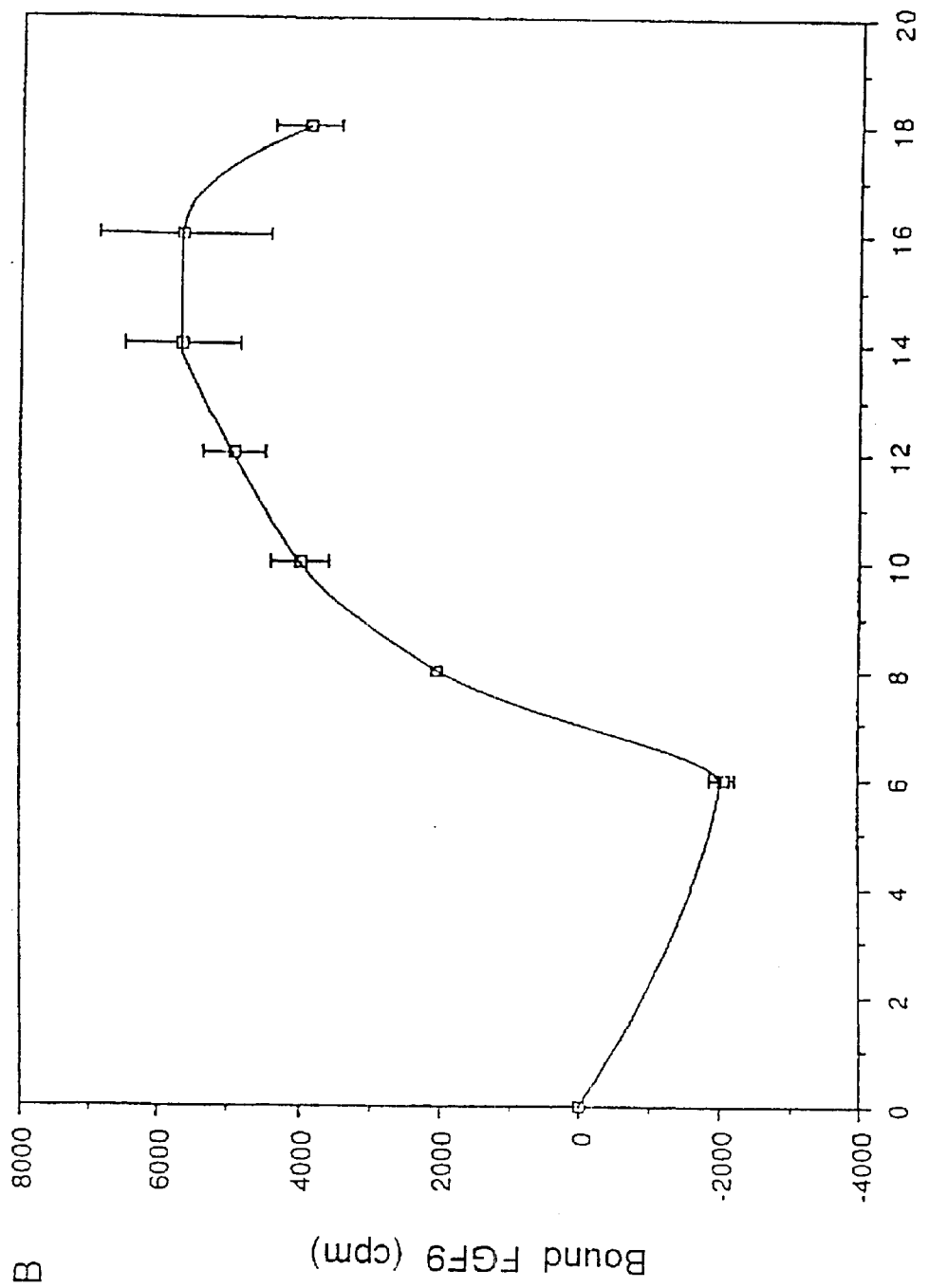

To study structural requirements of heparin for promoting FGF9 binding, we analyzed the effects of a series of heparin fragments ranging in size from 6 to 18 monosaccharide units, on FGF9 induced DNA synthesis. While a 6 mer heparin fragment inhibited the effect of FGF9, induction of DNA synthesis is observed with 8–10 mer fragments with maximal effect of FGF9 in the presence of 14–16 mer heparin fragments (FIG. 8B). These results indicate that a specific heparin size is required for activation of FGFR3 by FGF9.

EXAMPLE 6

Plasmid Construct for the Expression of FGF9

For the expression of recombinant FGF9, the mouse FGF9 cDNA was sub-cloned using the Ndel/BamH sites of the bacterial expression vector pET-3C. After transformation of BL-21 cells and induction with 1 mM of IPTG, the cells were lysed and FGF9 was purified on a heparin-sepharose column.

Full length mouse FGF9 cDNA was subcloned downstream of a splice acceptor site from the collagen IIA1 gene following the collagen IIA1 promoter and cartilage specific enhancer. This construct was linearized and used for injection into fertilized mice eggs for the generation of transgenic mice.

EXAMPLE 7

Transgenic Animal with Over Expression of FGF9

Transgenic mice transformed by the vector as described above feature an over-expression of FGF9. The phenotype of these transgenic mice is very similar to that of transgenic mice with FGFR3-Ach mutation (having the FGFR3 mutation of achondroplasia) characterized by an exceptionally small body size with a short tail and short hindlimbs. Such transgenic mice may serve as a model for various types of dwarfism as well as a model for abnormalities resulting from an excess of FGF9.

What is claimed is:

1. A method for stimulating cartilage or bone repair, the method comprising administering fibroblast growth factor 9 (FGF9) to a region of bone or cartilage requiring repair.

2. The method of claim 1, further comprising administering to the region heparin or a fragment of heparin with the ability to enhance binding of FGF9 to FGFR3.

3. The method of claim 1, wherein the FGF9 is mouse FGF9.

4. The method of claim 1, wherein the FGF9 is chicken FGF9.

5. The method of claim 1, wherein the FGF9 is human FGF9.

6. A pharmaceutical composition for modulating the activity of fibroblast growth factor receptor 3 (FGFR3), the composition comprising a pharmaceutically acceptable carrier and, as an active ingredient, chicken fibroblast growth factor 9 (FGF9).

7. A composition comprising a pharmaceutically acceptable carrier and, as active ingredients, chicken fibroblast growth factor 9 (FGF9) and heparin or a fragment of heparin with the ability to enhance binding of the FGF9 to fibroblast growth factor receptor 3 (FGFR3).

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 682 base pairs
      (B) TYPE: nucleic acid
      (C) STRANDEDNESS: single
      (D) TOPOLOGY: linear (xi) SEQUENCE DESCRIPTION: SEQ ID NO: 1:

```
ACAACGGTTT CCCTCTAGAA ATAATTTTGT TTAACTTTAA GAAGGAGATA TACATATGGC      60

TCCCTTAGGT GAAGTTGGGA GCTATTTCGG TGTGCAGGAC GCGGTACCGT TCGGGAACGT     120

ACCGGTGTTG CCGGTGGACA GTCCGGTGTT GCTAAGTGAC CACCTGGGTC AGTCCGAAGC     180

AGGGGGGCTG CCCCGGGGCC CCGCAGTCAC GGACTTGGAT CATTTAAAGG GGATTCTCAG     240

GCGGAGGCAG CTGTACTGCA GGACTGGATT TCATTTAGAG ATCTTCCCCA ACGGTACTAT     300

CCAGGGAACC AGGAAAGACC ACAGCCGCTT CGGCATTCTG GAATTTATCA GTATAGCAGT     360

GGGCCTGGTC AGCATTCGCG GTGTGGACAG TGGACTCTAC CTCGGCATGA ACGAGAAGGG     420

GGAGCTGTAT GGATCAGAAA AACTAACACA GGAATGTGTG TTCAGAGAAC AGTTTGAAGA     480

GAACTGGTAC AACACCTACT CTTCCAACCT CTATAAACAT GTGGACACCG GAAGGAGATA     540

CTATGTTGCA TTAAATAAGG ACGGGACTCC AAGAGAAGGG ACCAGGACTA AACGGCACCA     600

GAAATTTACA CATTTTTTAC CTAGACCAGT GGACCCTGAC AAAGTACCTG AACTATATAA     660
```

```
GGATATTCTA AGCCAAAGTT GA                                                682
```

(2) INFORMATION FOR SEQ ID NO: 2:

(i) SEQUENCE CHARACTERISTICS:
        (A) LENGTH: 627 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Mus pahari (xi) SEQUENCE DESCRIPTION: SEQ ID NO: 2:

```
ATGGCTCCCT TAGGTGAAGT TGGGAGCTAT TTCGGTGTGC AGGACGCGGT ACCGTTCGGG    60
AACGTACCGG TGTTGCCGGT GGACAGTCCG GTGTTGCTAA GTGACCACCT GGGTCAGTCC   120
GAAGCAGGGG GGCTGCCCCG GGGCCCCGCA GTCACGGACT TGGATCATTT AAAGGGGATT   180
CTCAGGCGGA GGCAGCTGTA CTGCAGGACT GGATTTCATT TAGAGATCTT CCCCAACGGT   240
ACTATCCAGG GAACCAGGAA AGACCACAGC CGCTTCGGCA TTCTGGAATT TATCAGTATA   300
GCAGTGGGCC TGGTCAGCAT TCGCGGTGTG GACAGTGGAC TCTACCTCGG CATGAACGAG   360
AAGGGGAGC TGTATGGATC AGAAAAACTA ACACAGGAAT GTGTGTTCAG AGAACAGTTT    420
GAAGAGAACT GGTACAACAC CTACTCTTCC AACCTCTATA AACATGTGGA CACCGGAAGG   480
AGATACTATG TTGCATTAAA TAAGGACGGG ACTCCAAGAG AAGGGACCAG GACTAAACGG   540
CACCAGAAAT TTACACATTT TTTACCTAGA CCAGTGGACC CTGACAAAGT ACCTGAACTA   600
TATAAGGATA TTCTAAGCCA AAGTTGA                                      627
```

(2) INFORMATION FOR SEQ ID NO: 3:

(i) SEQUENCE CHARACTERISTICS:
        (A) LENGTH: 208 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Mus pahari (xi) SEQUENCE DESCRIPTION: SEQ ID NO: 3:

```
Met Ala Pro Leu Gly Glu Val Gly Ser Tyr Phe Gly Val Gln Asp Ala
1               5                  10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Leu Pro Arg Gly
        35                  40                  45

Pro Ala Val Thr Asp Leu Asp His Leu Lys Gly Ile Leu Arg Arg Arg
        50                  55                  60

Gln Leu Tyr Cys Arg Thr Gly Phe His Leu Glu Ile Phe Pro Asn Gly
65              70                  75                  80

Thr Ile Gln Gly Thr Arg Lys Asp His Ser Arg Phe Gly Ile Leu Glu
            85                  90                  95
```

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205

(2) INFORMATION FOR SEQ ID NO: 4:

(i) SEQUENCE CHARACTERISTICS:
        (A) LENGTH: 660 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Gallus domesticus (xi) SEQUENCE DESCRIPTION: SEQ ID NO: 4:

CCGCGGGATT GGGAATTCCA TATGGCTCCC TTAGGTGAAG TCGGGAACTA TTTCGGTGTG      60

CAGGACGCGG TGCCCTTTGG GAACGTGCCC GCGCTGCCGG CGGACAGCCC GGTTTTGCTC     120

AGTGACCACC TGGGCCAGGC TGAGGCAGGT GGGCTGCCCA GGGGCCCCGC GGTCACGGAC     180

TTGGACCATT TAAAGGGGAT CCTCAGGAGG AGGCAGCTTT ACTGCAGGAC TGGATTTCAT     240

TTAGAAATCT TCCCCAATGG TACTATCCAG GGCACCAGGC AAGACCACAG CCGATTCGGT     300

ATACTGGAGT TCATCAGTAT AGCAGTGGGC CTGGTCAGCA TCCGAGGAGT AGACAGCGGA     360

CTCTACCTTG GAATGAATGA GAAAGGGGAG CTCTACGGCT CGGAAAAATT AACCCAGGAG     420

TGTGTATTCA GAGAGCAGTT TGAAGAAAAC TGGTATAACA CATATTCATC AAATCTATAT     480

AAACACGTGG ACACTGGAAG ACGATACTAC GTGGCGTTAA ATAAAGATGG AACTCCAAGA     540

GAAGGGACTA GGACTAAACG GCATCAAAAA TTTACACATT TTTCACCTAG ACCAGTGGAC     600

CCTGAGAAAG TACCTGAACT ATATAAGGAT ATTCTAAGCC AAAGTTGAGG ATCCCGAATC     660

(2) INFORMATION FOR SEQ ID NO: 5:

(i) SEQUENCE CHARACTERISTICS:
        (A) LENGTH: 220 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Gallus domesticus (xi) SEQUENCE DESCRIPTION: SEQ ID NO: 5:

-continued

```
Pro Arg Asp Trp Glu Phe His Met Ala Pro Leu Gly Glu Val Gly Asn
1               5                   10                  15

Tyr Phe Gly Val Gln Asp Ala Val Pro Phe Gly Asn Val Pro Ala Leu
            20                  25                  30

Pro Ala Asp Ser Pro Val Leu Leu Ser Asp His Leu Gly Gln Ala Glu
            35                  40                  45

Ala Gly Gly Leu Pro Arg Gly Pro Ala Val Thr Asp Leu Asp His Leu
    50                  55                  60

Lys Gly Ile Leu Arg Arg Arg Gln Leu Tyr Cys Arg Thr Gly Phe His
65                  70                  75                  80

Leu Glu Ile Phe Pro Asn Gly Thr Ile Gln Gly Thr Arg Gln Asp His
                85                  90                  95

Ser Arg Phe Gly Ile Leu Glu Phe Ile Ser Ile Ala Val Gly Leu Val
            100                 105                 110

Ser Ile Arg Gly Val Asp Ser Gly Leu Tyr Leu Gly Met Asn Glu Lys
            115                 120                 125

Gly Glu Leu Tyr Gly Ser Glu Lys Leu Thr Gln Glu Cys Val Phe Arg
    130                 135                 140

Glu Gln Phe Glu Glu Asn Trp Tyr Asn Thr Tyr Ser Ser Asn Leu Tyr
145                 150                 155                 160

Lys His Val Asp Thr Gly Arg Arg Tyr Tyr Val Ala Leu Asn Lys Asp
                165                 170                 175

Gly Thr Pro Arg Glu Gly Thr Arg Thr Lys Arg His Gln Lys Phe Thr
                180                 185                 190

His Phe Ser Pro Arg Pro Val Asp Pro Glu Lys Val Pro Glu Leu Tyr
                195                 200                 205

Lys Asp Ile Leu Ser Gln Ser Xaa Gly Ser Arg Ile
    210                 215                 220
```

(2) INFORMATION FOR SEQ ID NO: 6:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO: 6:

```
Cys Ser Asn Leu Tyr Lys His Val Gln Thr Gly Arg Arg Tyr
1               5                   10
```

(2) INFORMATION FOR SEQ ID NO: 7:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO: 7:

```
Asp His Leu Lys Gly Ile Leu Arg Arg Arg Gln Leu Tyr Cys
1               5                   10
```

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 8:

GGGAATTCCA TATGGCTCCC TTAGGTGAAG         30

(2) INFORMATION FOR SEQ ID NO: 9:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO: 9:

CGGGATCCTC AACTTTGGCT TAGAATATCC         30

(2) INFORMATION FOR SEQ ID NO: 10:

(i) SEQUENCE CHARACTERISTICS:
      (A) LENGTH: 208 amino acids
      (B) TYPE: amino acid
      (C) STRANDEDNESS: single
      (D) TOPOLOGY: linear (ii) MOLECULE TYPE: protein (vi) ORIGINAL SOURCE:
      (A) ORGANISM: Rattus norvegicus (xi) SEQUENCE DESCRIPTION: SEQ ID NO: 10:

```
Met Ala Pro Leu Gly Glu Val Gly Ser Tyr Phe Gly Val Gln Asp Ala
1               5                  10                  15

Val Pro Phe Gly Asn Val Pro Leu Pro Val Asp Ser Pro Val Leu
                20                  25                  30

Leu Ser Asp His Leu Gly Gln Ser Glu Ala Gly Gly Leu Pro Arg Gly
                35                  40                  45

Pro Ala Val Thr Asp Leu Asp His Leu Lys Gly Ile Leu Arg Arg Arg
        50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
                100                 105                 110

Gly Leu Tyr Leu Gly Met Asn Glu Lys Gly Glu Leu Tyr Gly Ser Glu
                115                 120                 125

Lys Leu Thr Gln Glu Cys Val Phe Arg Glu Gln Phe Glu Glu Asn Trp
        130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
                180                 185                 190

Asp Pro Asp Lys Val Pro Glu Leu Tyr Lys Asp Ile Leu Ser Gln Ser
                195                 200                 205
```

(2) INFORMATION FOR SEQ ID NO: 11:

(i) SEQUENCE CHARACTERISTICS:
       (A) LENGTH: 208 amino acids
       (B) TYPE: amino acid
       (C) STRANDEDNESS: single
       (D) TOPOLOGY: linear (ii) MOLECULE TYPE: protein (vi) ORIGINAL SOURCE:
       (A) ORGANISM: Homo sapiens (xi) SEQUENCE DESCRIPTION: SEQ ID NO: 11:

Met Ala Pro Leu Gly Glu Val Gly Asn Tyr Phe Gly Val Gln Asp Ala
1               5                  10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
            35                  40                  45

Pro Ala Val Thr Asp Leu Asp His Leu Lys Gly Ile Leu Arg Arg Arg
        50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
                100                 105                 110

Gly Leu Tyr Leu Gly Met Asn Glu Lys Gly Glu Leu Tyr Gly Ser Glu
            115                 120                 125

Lys Leu Thr Gln Glu Cys Val Phe Arg Glu Gln Phe Glu Glu Asn Trp
130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205

(2) INFORMATION FOR SEQ ID NO: 12:

(i) SEQUENCE CHARACTERISTICS:
        (A) LENGTH: 627 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Rattus norvegicus (xi) SEQUENCE DESCRIPTION: SEQ ID NO: 12:

ATGGCTCCCT TAGGTGAAGT TGGGAGCTAT TTCGGTGTGC AGGACGCGGT ACCGTTCGGG    60

AACGTACCGG TGTTGCCGGT GGACAGTCCG GTGTTGCTAA GTGACCACCT GGGTCAGTCC   120

GAAGCAGGGG GGCTGCCCCG GGACCCGCA GTCACGGACT TGGATCATTT AAAGGGGATT   180

CTCAGGCGGA GGCAGCTGTA CTGCAGGACT GGATTTCACT TAGAAATCTT CCCCAACGGT   240

-continued

```
ACTATCCAGG GAACCAGGAA AGACCACAGC CGATTCGGCA TTCTGGAATT TATCAGTATA    300

GCAGTGGGCC TGGTCAGCAT TCGTGGTGTG GACAGTGGAC TCTACCTCGG CATGAACGAG    360

AAGGGGGAGC TGTATGGATC AGAAAAACTA ACACAGGAGT GCGTGTTCAG AGAACAGTTT    420

GAAGAAAACT GGTACAACAC CTACTCTTCC AACCTGTACA AGCACGTGGA CACCGGAAGG    480

AGATACTATG TTGCATTAAA TAAGGATGGG ACTCCAAGAG AAGGGACCAG GACTAAACGG    540

CACCAGAAAT TTACACATTT TTTACCTAGA CCAGTGGACC CTGACAAAGT ACCTGAACTA    600

TATAAGGATA TTCTAAGCCA AAGTTGA                                       627

(2) INFORMATION FOR SEQ ID NO: 13:

(i) SEQUENCE CHARACTERISTICS:
        (A) LENGTH: 627 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO: 13:

ATGGCTCCCT TAGGTGAAGT TGGGAACTAT TTCGGTGTGC AGGATGCGGT ACCGTTTGGG     60

AATGTGCCCG TGTTGCCGGT GGACAGCCCG GTTTTGTTAA GTGACCACCT GGGTCAGTCC    120

GAAGCAGGGG GGCTCCCCAG GGGACCCGCA GTCACGGACT TGGATCATTT AAAGGGGATT    180

CTCAGGCGGA GGCAGCTATA CTGCAGGACT GGATTTCACT TAGAAATCTT CCCCAATGGT    240

ACTATCCAGG GAACCAGGAA AGACCACAGC CGATTTGGCA TTCTGGAATT TATCAGTATA    300

GCAGTGGGCC TGGTCAGCAT TCGAGGCGTG GACAGTGGAC TCTACCTCGG GATGAATGAG    360

AAGGGGGAGC TGTATGGATC AGAAAAACTA ACCCAAGAGT GTGTATTCAG AGAACAGTTC    420

GAAGAGAACT GGTATAATAC GTACTCGTCA AACCTATATA AGCACGTGGA CACTGGAAGG    480

CGATACTATG TTGCATTAAA TAAAGATGGG ACCCCGAGAG AAGGGACTAG GACTAAACGG    540

CACCAGAAAT TCACACATTT TTTACCTAGA CCAGTGGACC CCGACAAAGT ACCTGAACTG    600

TATAAGGATA TTCTAAGCCA AAGTTGA                                       627
```